United States Patent [19]
Filby et al.

[11] 3,950,404
[45] Apr. 13, 1976

[54] METHOD FOR PREPARATION OF SULFINIC ACIDS
[75] Inventors: Gordon Filby, Karlsruhe; Kirsten Günther, Spock; Ralf-Dieter Penzhorn, Neuthard, all of Germany
[73] Assignee: Gesellschaft fur Kernforschung mbH, Karlsruhe, Germany
[22] Filed: Apr. 30, 1974
[21] Appl. No.: 465,565

[30] Foreign Application Priority Data
May 3, 1973 Germany............................ 2322199

[52] U.S. Cl. ............................................. 260/513.7
[51] Int. Cl.² ........................................ C07C 145/00
[58] Field of Search ................................. 260/513.7

[56] References Cited
UNITED STATES PATENTS
3,329,708  7/1967  Berger ............................ 260/513.7

Primary Examiner—James O. Thomas, Jr.
Assistant Examiner—Nicky Chan
Attorney, Agent, or Firm—Spencer & Kaye

[57] ABSTRACT

Sulfinic acids are prepared by forming a reaction mixture from a first solution made by dissolving an organic compound containing a sulfhydryl group bound to a carbon in a solvent which is inert and readily volatile at room temperature and a second solution made by dissolving a weak oxidation agent in a solvent which is inert and readily volatile at room temperature. The reaction mixture is maintained at a temperature lower than room temperature and the organic sulfhydryl containing compound is oxidized to a sulfinic acid and the oxidation agent is reduced in the reaction mixture. The reduced oxidation agent is removed from the reaction mixture and then the solvent is blown out from the reaction mixture at room temperature with a stream of inert gas.

13 Claims, No Drawings

METHOD FOR PREPARATION OF SULFINIC ACIDS

BACKGROUND OF THE INVENTION

The present invention relates to a method for preparing high purity sulfinic acids.

Many methods have been employed to produce sulfinic acids. One of the most widely used methods is the reduction of sulfonyl halogenides with, for example, zinc, iron, aluminum or magnesium. The product yields from this reduction method, however, are low and the products themselves require additional processing to produce the desired sulfinic acids because the reduction partially goes beyond the sulfinic acids to disulfides or mercaptans.

Oxidation methods where sulfur containing organic compounds are oxidized also have been used to produce sulfinic acids, but these oxidation methods are among the less popular methods that have been used to produce sulfinic acids. For example, in one known oxidation method sodium thioethylate ($C_2H_5$—SNa) has been oxidized with dry oxygen. In another prior art oxidation method, sulfhydryl groups containing substituted aromatic or heterocyclic compounds have been treated with chlorine, an alkali potassium permanganate solution or with a 30% solution of hydrogen peroxide. In still another oxidation method, aryl sulfacids have been brought in contact with air, an alkali medium or potassium hexacyanoferrate (III). All prior art oxidation methods, however, have the drawback that the oxidation reactions cannot be controlled and thus a partial further oxidation of the sulfinic acids to sulfonic acids occurs and cannot be avoided. Accordingly, in the prior art oxidation methods, it is necessary to use further time consuming and relatively complicated processing techniques such as an additional processing method for treating the mixture to convert the sulfonic acid and form sulfinic acid or a method for separating the sulfinic acids from the sulfonic acids.

SUMMARY OF THE INVENTION

It is therefore a primary object of the present invention to provide a method which avoids the drawbacks of the known methods, i.e. to provide a method which eliminates the simultaneous formation of compounds of higher or lower oxidation stages (e.g. sulfonic acids or disulfides and mercaptans) than that of the desired sulfinic acid. Another object of the invention is to produce sulfinic acids in high purity and in a heavy yield without there being necessary any additional processing or separating procedures.

To achieve the foregoing objects and in accordance with its purpose, the present invention provides a method for preparing high purity a sulfinic acid which comprises: dissolving an organic compound which contains a sulfhydryl group bound to a carbon atom in a solvent which is inert and readily volatile at room temperature to form a first solution; dissolving a weak oxidation agent in a solvent which is inert and readily volatile at room temperature to form a second solution; bringing the organic sulfhydryl containing compound into intimate contact with the oxidation agent at a temperature below room temperature to oxidize the organic sulfhydryl containing compound to a sulfinic acid and reduce the oxidation agent by adding the first and second solutions together to form a reaction mixture; removing from the reaction mixture the reduced oxidation agent formed during the oxidation; and then blowing out the solvent of the first solution and the solvent of the second solution from the reaction mixture at room temperature with a stream of inert gas.

GENERAL ASPECTS OF THE PRESENT INVENTION

The process of the present invention provides a controlled oxidation of an organic sulfhydryl containing compound with a weak oxidation agent to produce a sulfinic acid without formation of sulfonic acids. The organic sulfhydryl containing compounds that can be used in the process of the present invention include compounds of the formula R—SH wherein R can be a hydrocarbon radical preferably selected from the group consisting of alkyl, aryl, alkylaryl, and arylalkyl radicals. The hydrocarbon radicals can contain from 2 to at least 6 carbon atoms and can be substituted with such groups as —COOH, —$NO_2$, and halogens. The aryl radicals can include single ring radicals or condensed ring radicals such as naphthylene.

When R is an alkyl radical, it preferably contains from 2 to 4 carbon atoms. Sulfinic acids can be obtained from all isomers of mercaptans having 2 to 4 carbon atoms. Phenyl radicals are preferred aryl containing radicals. Exemplary of suitable organic sulfhydryl containing compounds are alkyl mercaptans such as ethyl mercaptan, propyl mercaptan, butyl mercaptan, and thiophenols such as phenyl mercaptan. Still other suitable organic sulfhydryl containing compounds are benzyl mercaptan, tolyl mercaptan, xylyl mercaptan, cumyl mercaptan and aromatic compounds bearing up to 6 side chain carbon atoms irrespective of the position of the SH-group in this chain.

The oxidation agents that can be used in the present invention to oxidize the organic sulfhydryl containing compound preferably are peroxy compounds such as organic peroxyacids and include m-chloroperoxy benzoic acid and peroxyacetic acid. As weak oxidation agents aromatic peroxyacids have the favorable advantage that firstly they are sufficiently weak that further oxidation to sulphonic acid is excluded and secondly the reduced product is insoluble in the solvents employed. Thus (drastic/hard) separation methods (removal of water etc.) which may be possibly lead to sulphonic acid decomposition can be avoided.

The organic sulfhydryl containing compound and the weak oxidation agent are dissolved in suitable solvents to form separate solutions of each of these reactants. The solvent for each reactant must be inert so that it does not interfere with or take part in the reaction. In addition, the solvent for each reactant must be readily volatile at room temperature so that it can be driven off easily from the reaction mixture after the reaction is completed. In a preferred embodiment of the invention, the solvent for forming the solution of organic sulfhydryl containing compound is the same as that used for forming the solution of weak oxidation agent. A suitable solvent that can be used for forming both these solutions is methylene chloride. Other solvents that can be used for forming the solutions of organic sulfhydryl containing compounds include chloroform, carbon tetrachloride, and the easily volatilized Freons i.e., the easily volatilized fluorocarbons. The same solvents can be used for forming the solution of weak oxidation agents.

The organic sulfhydryl containing compound and oxidation agent are preferably reacted with each other in stoichiometric amount. The use of stoichiometric quantities enables a product of high purity and yield to be obtained uncontaminated by products of a higher or lower oxidation state.

After the two reactant solutions are formed they are cooled to and maintained at a low temperature below room temperature in suitable cooling apparatus. Preferably, each solution is cooled to between −30° C and −80° C. The cooled solutions are then added together to bring the weak oxidation agent into intimate contact with the organic sulfhydryl containing compound and form a reaction mixture which is maintained at the low temperature. The oxidation agent thus contacts and oxidizes the organic sulfhydryl containing compound to its corresponding sulfinic acid. The low temperature of the reaction mixture controls the oxidation reaction and enables the organic sulfhydryl containing compound to be oxidized to sulfinic acid without further oxidation of the resulting sulfinic acid to sulfonic acid. The low temperature prevents the solvent in the first solution and the solvent in the second solution from volatilizing and prevents the sulfinic acid from being oxidized to a sulfonic acid. In a preferred embodiment of the invention, the solution of oxidation agent is added in portions over a period of time to the solution of organic sulfhydryl containing compound under heavy stirring. After addition of the last portion, the reaction mixture is left to stand for 3 to 12 hours to ensure completion of the reaction.

During the oxidation reaction, the oxidation agent is reduced and forms a precipitate in the reaction mixture. This precipitate preferably is filtered out from the reaction mixture after the mixture has been left to stand for a time to ensure completion of the reaction. After the first filtration, the reaction mixture can be cooled to a low temperature of about −80° C and then quickly filtered to remove remaining traces of any precipitate or other solids. The reaction products produced from the oxidation agent thus are removed from the reaction mixture. The reaction mixture then can be brought to room temperature and the solvent or solvents in the mixture can be blown out by a stream of inert gas such as nitrogen to leave the pure sulfinic acid. Other inert gases that can be used include carbon dioxide and the noble gases.

In one preferred embodiment of the present invention, a mercaptan, dissolved in methylene chloride, is brought to a controlled reaction in a temperature range between −30° C and −80° C with a stoichiometric quantity of m-chloroperoxy benzoic acid (MCPBA) dissolved in methylene chloride and the resulting m-chlorobenzoic acid (MCBA) is filtered out quickly.

In another preferred embodiment of the present invention a thiophenol dissolved in methylene chloride is gradually mixed in batches and in a temperature range between −30° and −80° C under heavy stirring with a stoichiometric quantity of MCPBA dissolved in methylene chloride, the resulting deposit of MCBA is quickly filtered out, the methylene chloride is removed at room temperature by means of a stream of nitrogen and the sulfinic acid which has thus been produced in high purity is strongly dried in an evacuated desiccator over phosphorus pentoxide for about half an hour.

The sulfinic acids produced by the present invention are extremely pure and do not contain any sulfonic acid. Therefore it is unnecessary to employ further processing techniques to deal with unwanted sulfonic acid. The sulfinic acids of the present invention have the formula R—SO.OH where R is as defined above.

The sulfinic acids which are not stable in air can be stored for months at −30° C and in a vacuum without noticeable decomposition or change in their purity control values as measured by combined mass spectrometry and gas chromatography. It has been found, however, that for long-time storage it is preferable to convert the sulfinic acids to their salts, particularly their silver salts, with subsequent storage of the salts at low temperatures in a vacuum.

Sulfinic acids are used, for example, as polymerization activators. Further, their occurrence as an intermediate product in photochemical smog systems are under consideration when the problems of air pollution are examined. The sulfinic acids produced according to the method of the present invention can serve as standard substances for quantitative control tests since their degree of purity is so high.

DESCRIPTION OF THE PREFERRED EMBODIMENTS

The present invention will be described below with several examples which, however, are not to be considered as limiting the invention.

EXAMPLE 1

A first solution is prepared by adding 10 ml methylene chloride to a first container at room temperature, dissolving 0.05 mol ethylmercaptan in the 10 ml of methylene chloride, and then cooling the first solution to −30° C in cooling apparatus. A second solution is prepared by adding 200 ml methylene chloride to a second container at room temperature, dissolving 0.1 mol MCPBA in the 200 ml of methylene chloride and then cooling the second solution to −30° C in cooling apparatus. At intervals of 30 minutes, 10 ml portions of the MCPBA solution are slowly pipetted into the mercaptan solution under heavy stirring and the containers are each immediately returned to the cooling apparatus. When the entire quantity of the MCPBA solution has been added, the reaction vessel is left to rest over night at −30° C. A precipitate of MCPA forms and this precipitate then is filtered out. In order to also remove any remaining traces of MCBA, the solution is cooled to about −80° C by means of liquid nitrogen and is then quickly filtered. If necessary, the cooling treatment to about −80° C is repeated. After removal of the MCBA, the reaction mixture is brought to room temperature and the solvent is blown out merely with the air of a fast flowing stream of nitrogen. The ethyl sulfinic acid remains as a light yellow oil or as a solid and is strongly dried for a short period of time (about 30 minutes) in an evacuated desiccator over $P_2O_5$ to remove any possibly remaining traces of moisture. The ethyl sulfinic acid yield lies in the range between 80 and 85% of the amount of mercaptan used. The infrared spectrogram of the final product shows no MCBA peaks. Further purity tests, for example a combined gas chromatographic mass spectrometric analysis of NMR spectrometry do not indicate any foreign substances in the freshly produced sulfinic acid end product.

A quantitative element analysis for carbon, hydrogen and sulfur produced the following analysis values for an ethylsulfinic acid charge: Calculated: 25.6% C 6.4% H 34.0% S. Analysis value: 25.1% C 6.2% H 34.4% S.

EXAMPLE 2

The procedure of Example 1 is repeated except that instead of the ethylmercaptan, 0.05 mol n-propylmercaptan is dissolved in 10 ml methylene chloride and is mixed, with 200 ml of a solution of 0.1 mol MCPBA.

A charge of an n-propylsulfinic acid end product produced in this manner was analyzed quantitatively for carbon, hydrogen and sulfur and resulted in the following analysis values: Calculated: 33.4% C 7.4% H 29.6% S. Analysis value: 33.6% C 6.9% H 29.9% S.

EXAMPLE 3

The procedure of Example 1 is repeated except that instead of using ethylmercaptan, n-butylmercaptan is converted to n-butyl sulfinic acid of high purity.

EXAMPLE 4

The procedure of Example 1, is repeated except that instead of using ethylmercaptan, phenyl mercaptan (thiophenol) is converted to benzosulfinic acid of high purity.

It will be understood that the above description of the present invention is susceptible to various modifications, changes and adaptations, and the same are intended to be comprehended within the meaning and range of equivalents of the appended claims.

We claim:

1. A method for preparing a high purity sulfinic acid, comprising
   a. dissolving an organic compound containing a sulfhydryl group bound to a carbon atom in a solvent which is inert and readily volatile at room temperature to form a first solution, said organic sulfhydryl containing compound being of the formula R—SH wherein R is a hydrocarbon radical selected from the group consisting of alkyl, aryl, alkylaryl, and arylalkyl radicals and said solvent being methylene chloride, chloroform, carbon tetrachloride or an easily volatilized fluorocarbon;
   b. dissolving a stoichiometric quantity of a weak oxidation agent in the form of m-chloroperoxy benzoic acid or peroxyacetic acid in a solvent which is inert and readily volatile at room temperature to form a second solution, said solvent being methylene chloride, chloroform, carbon tetrachloride or an easily volatilized fluorocarbon;
   c. bringing the organic sulfhydryl containing compound into intimate contact with the oxidation agent at a temperature of from about −30° C to about −80° C to oxidize the organic sulfhydryl containing compound to a sulfinic acid and reduce the oxidation agent by adding the first and second solutions together to form a reaction mixture;
   d. removing from the reaction mixture the reduced oxidation agent formed during the oxidation; and
   e. thereafter blowing the solvent out from the reaction mixture at room temperature with a stream of inert gas.

2. The method according to claim 1 wherein a mercaptan is dissolved in methylene chloride and brought to a controlled reaction in a temperature range between −30° and −80° C with a stoichiometric quantity of m-chloroperoxy benzoic acid dissolved in methylene chloride and the resulting m-chlorobenzoic acid is quickly filtered out.

3. The method according to claim 2 wherein the mercaptan contains from 2 to 4 carbon atoms.

4. The method according to claim 1 wherein a thiophenol dissolved in methylene chloride is gradually mixed, in batches, in a temperature range between −30° and −80° C and under heavy stirring with a stoichiometric quantity of m-chloroperoxy benzoic acid dissolved in methylene chloride, the resulting precipitate of m-chlorobenzoic acid is quickly filtered out, and the methylene chloride is removed at room temperature by means of a stream of nitrogen to obtain sulfinic acid in high purity.

5. The method according to claim 4 wherein the high purity sulfinic acid is strongly dried in an evacuated desiccator over phosphorus pentoxide for approximately half an hour.

6. The method according to claim 1 wherein the organic sulfhydryl containing compound is a mercaptan containing from 2 to 4 carbon atoms.

7. The method according to claim 6 wherein the mercaptan is ethyl mercaptan.

8. The method according to claim 6 wherein the mercaptan is propyl mercaptan.

9. The method of claim 6 wherein the mercaptan is butyl mercaptan.

10. The method of claim 1 wherein the organic sulfhydryl containing compound is a thiophenol.

11. The method according to claim 1 wherein the reaction is carried out at a temperature which prevents the solvent in the first solution and the solvent in the second solution from volatilizing and prevents the sulfinic acid from being oxidized to a sulfonic acid.

12. The method according to claim 1 wherein the solvent for the first solution and for the second solution is methylene chloride.

13. The method according to claim 1 wherein the organic compound is selected from the group consisting of alkyl mercaptans containing from 2 to 4 carbon atoms and thiophenols with or without side chains containing up to 6 side chain carbon atoms.

* * * * *